(12) United States Patent
Paek et al.

(10) Patent No.: US 7,915,397 B2
(45) Date of Patent: Mar. 29, 2011

(54) PROMOTOR OF HOT PEPPER WHICH IS RELATED TO TMV-RESISTANCE

(75) Inventors: Kyung-Hee Paek, Seoul (KR); Boo-Ja Lee, Daegu (KR); Ki-Jeong Kim, Kyungbook Province (KR); Soo Bok Choi, Seoul (KR)

(73) Assignee: Korea University Industry and Academy Cooperation Foundation, Gyeonggi-Do (KR)

( * ) Notice: Subject to any disclaimer, the term of this patent is extended or adjusted under 35 U.S.C. 154(b) by 72 days.

(21) Appl. No.: 12/026,464

(22) Filed: Feb. 5, 2008

(65) Prior Publication Data

US 2009/0199310 A1    Aug. 6, 2009

(51) Int. Cl.
*C12N 15/63* (2006.01)
*C12N 15/82* (2006.01)
*C12N 15/87* (2006.01)
*C12N 15/00* (2006.01)

(52) U.S. Cl. ..... 536/24.1; 800/278; 800/287; 435/320.1

(58) Field of Classification Search ........................ None
See application file for complete search history.

(56) References Cited

U.S. PATENT DOCUMENTS

2004/0031072 A1 * 2/2004 La Rosa et al. ............... 800/278

OTHER PUBLICATIONS

Lee, Boo-Ja (Feb. 2007) Molecular Characterization of Defense-Related Genes in Response to Tobacco mosaic virus in Hot Pepper Plant by Proteomics and Promoter Analyses, Thesis(Doctor), Korea University.
Lee, Boo-Ja et al. (Sep. 9-13, 2007) Tobacco Mosaic Virus-Induced Transcriptional Activation of Hot Pepper Pathogenesis-Related Protein 4 (CaPR-4) via Binding of Dof Transcription Factor to TMV-Inducible Cis-Acting Elements within its Promoter in Hot Pepper, The 4th Solanaceae Workshop 2007.
Hong, J.K. et al. (Aug. 15, 2005) Activation of Pepper Basic PR-1 Gene Promoter During Defense Signaling to Pathogen, Abiotic and Environmental Stresses, Gene:356:169-180.
Buchel, A.S. et al (1999) Mutation of GT-1 Binding Sites in the Pr-1A Promoter Influences the Level of Inducible Gene Expression In Vivo, Plant Molecular Biology 40:387-396.

* cited by examiner

Primary Examiner — Li Zheng
(74) *Attorney, Agent, or Firm* — Greenlee Sullivan P.C.

(57) ABSTRACT

The present invention relates to a promoter of hot pepper related to TMV-resistance, more precisely a promoter of the gene related to TMV-resistance and a method for regulating the expression of a target protein by using a transcription factor binding to the same. The method of the present invention can be effectively used for the regulation of the expression of a target protein in disease-resistant plants.

7 Claims, 8 Drawing Sheets

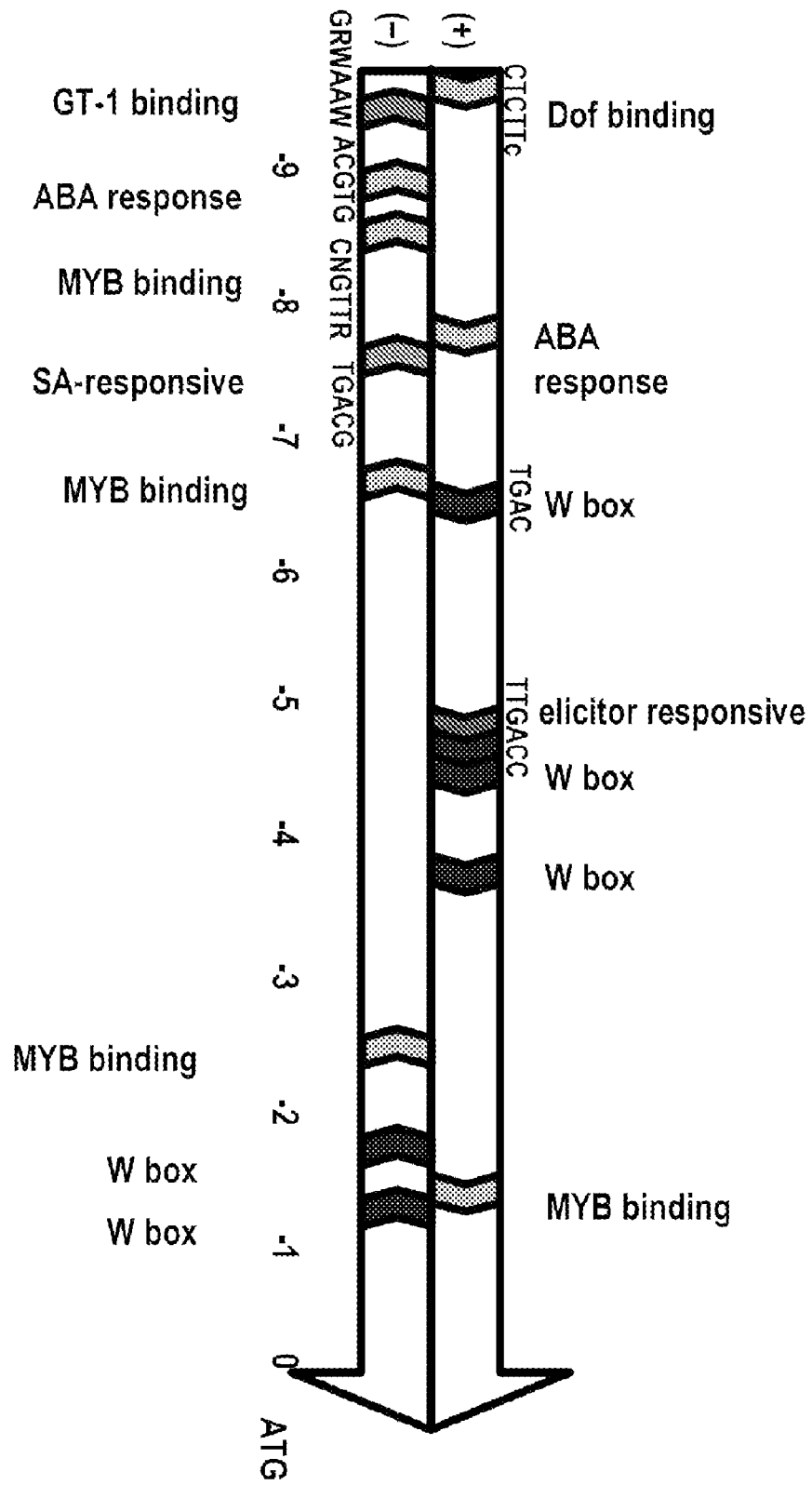
[Fig. 1]

[Fig. 2]
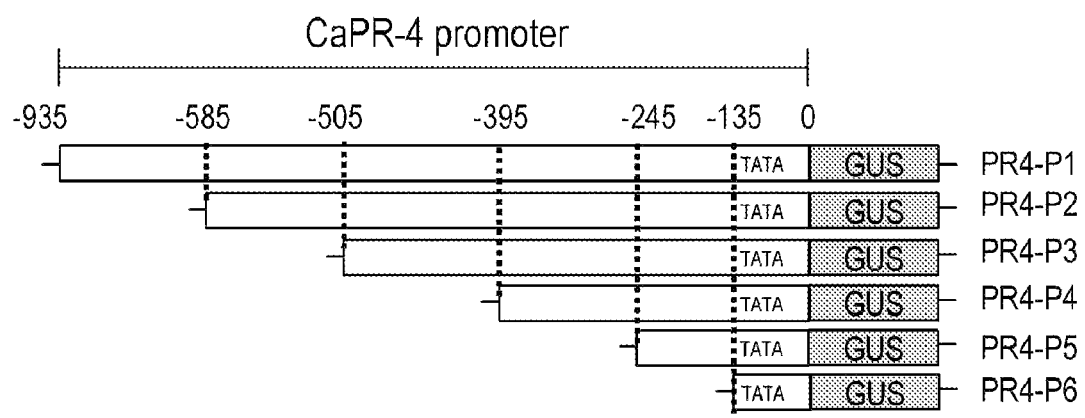
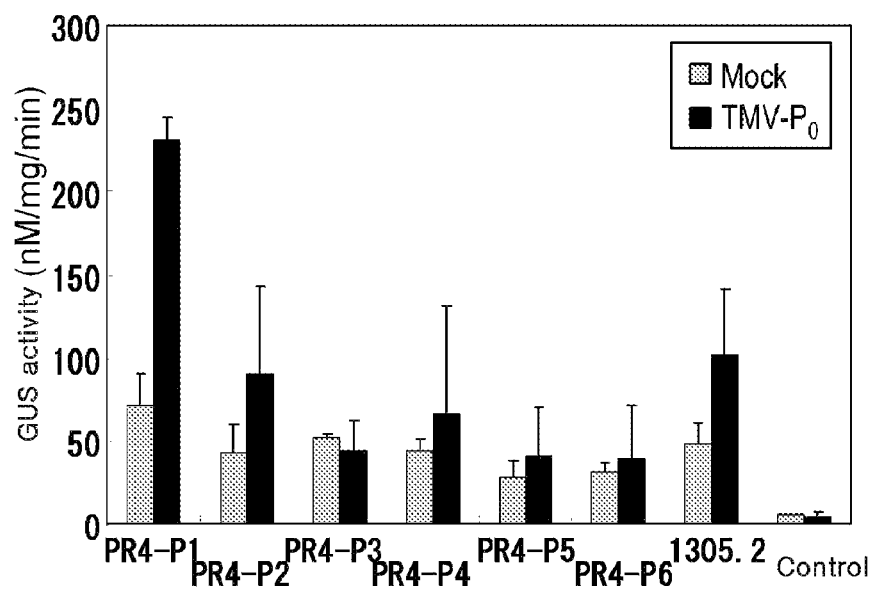

[Fig. 3]
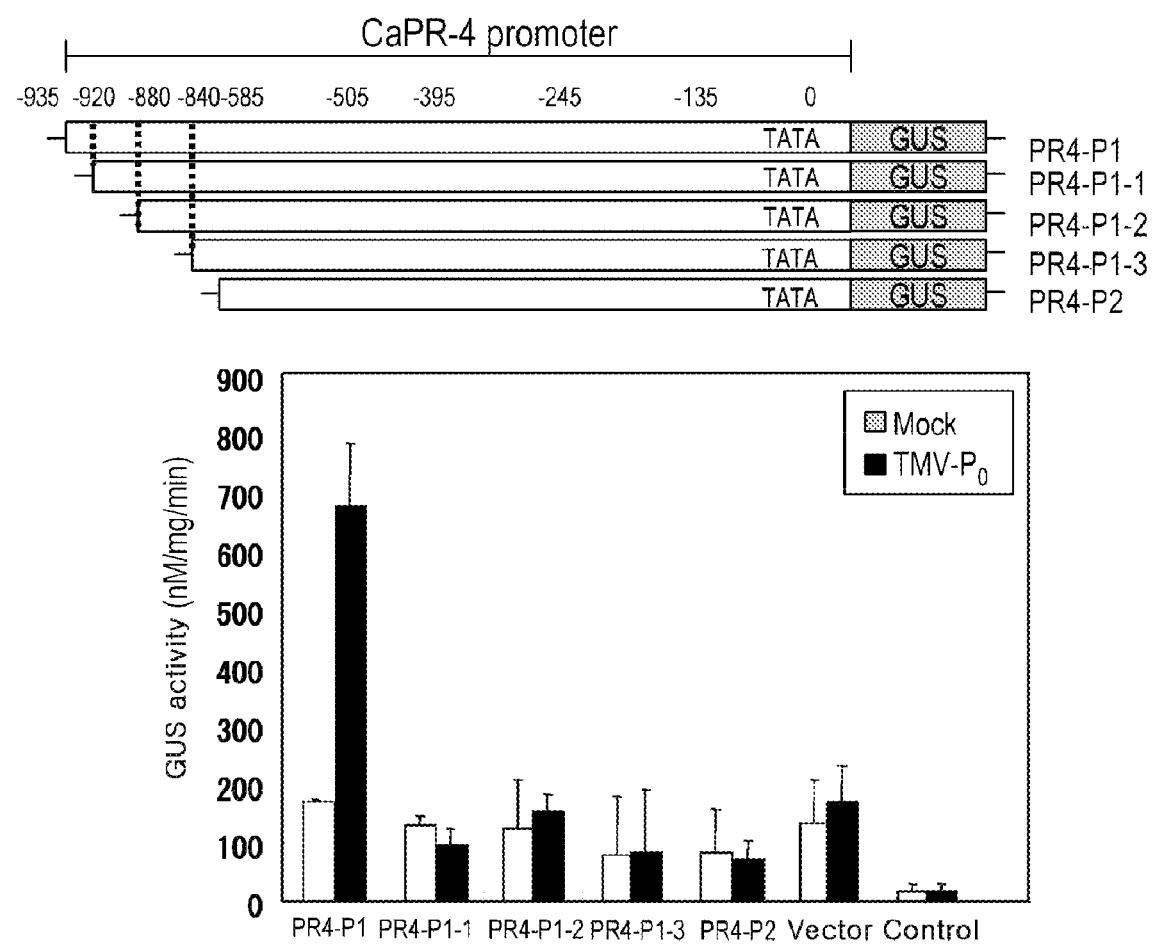

[Fig. 4]
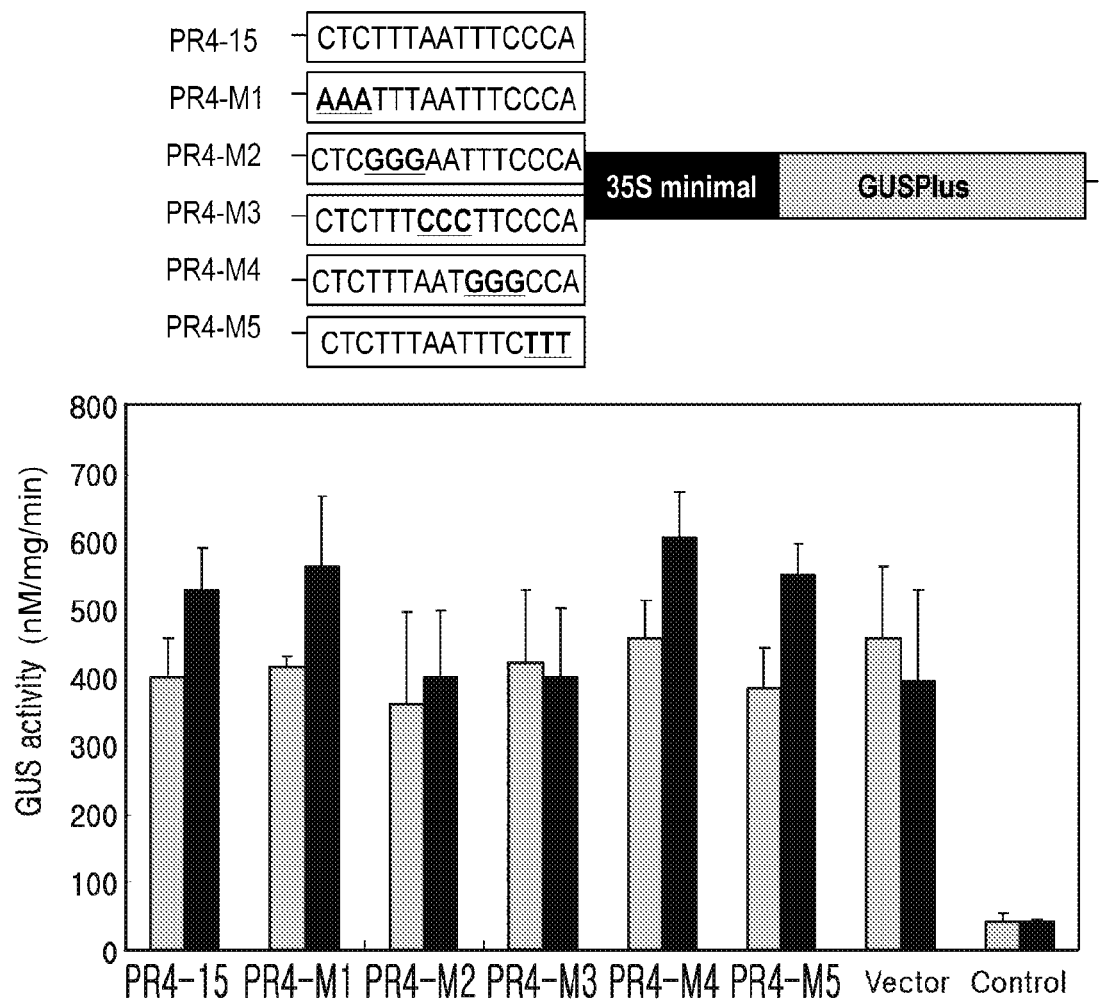

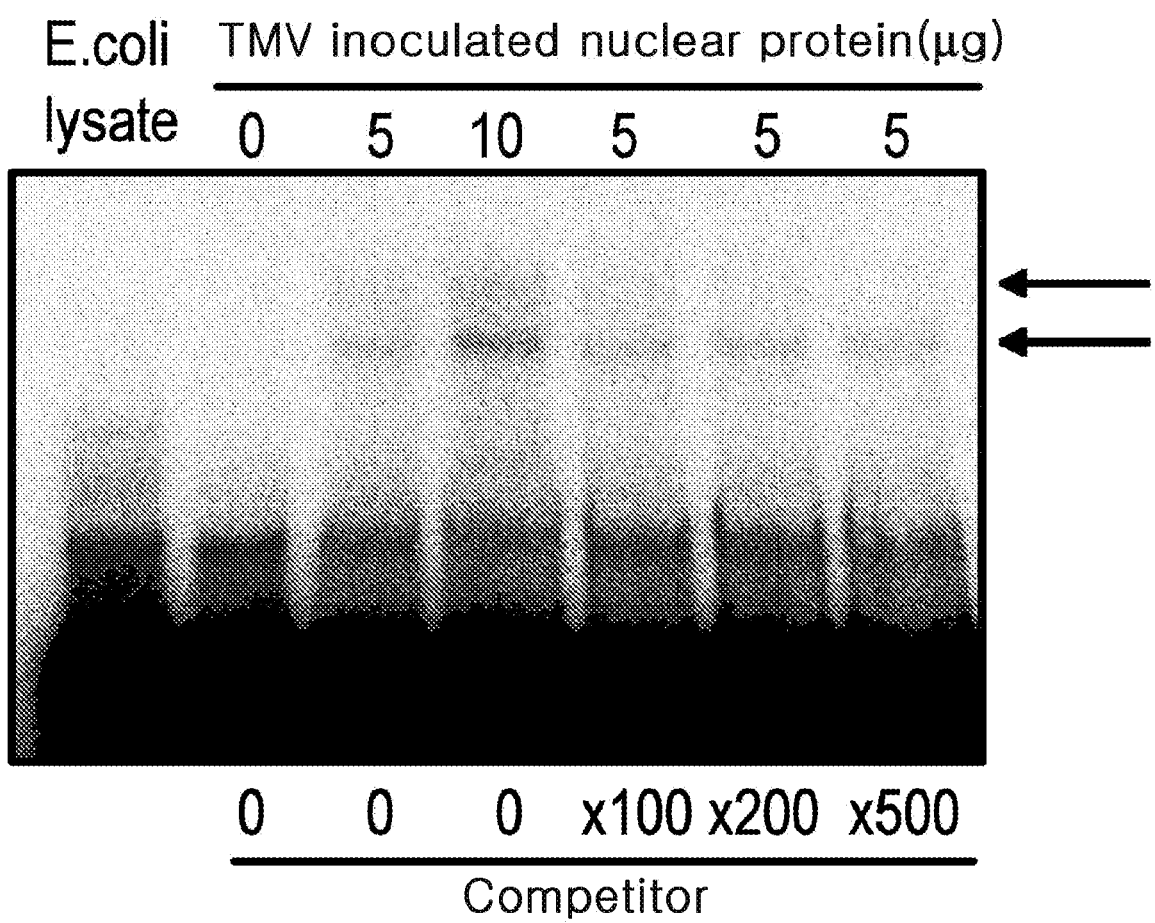
[Fig. 6]

[Fig. 7]
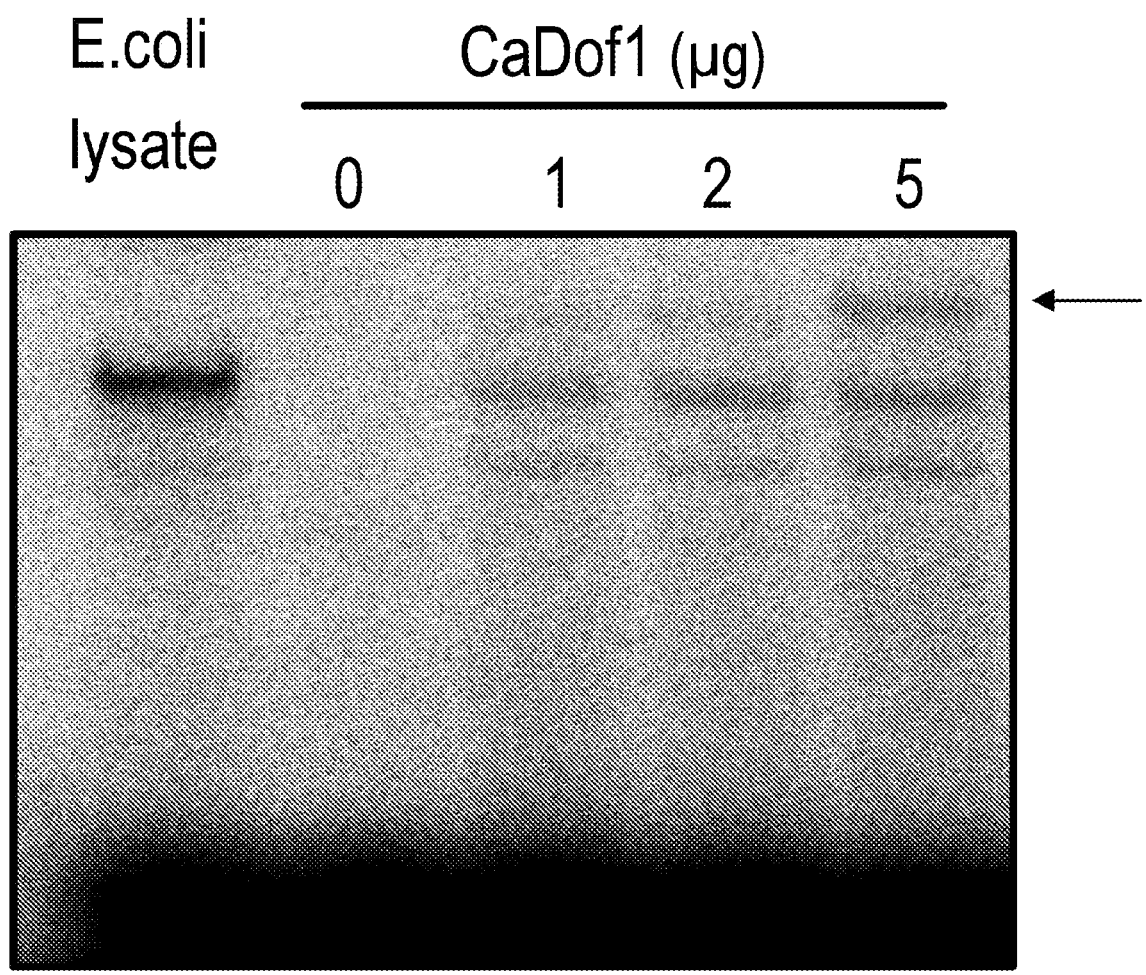

[Fig. 8]
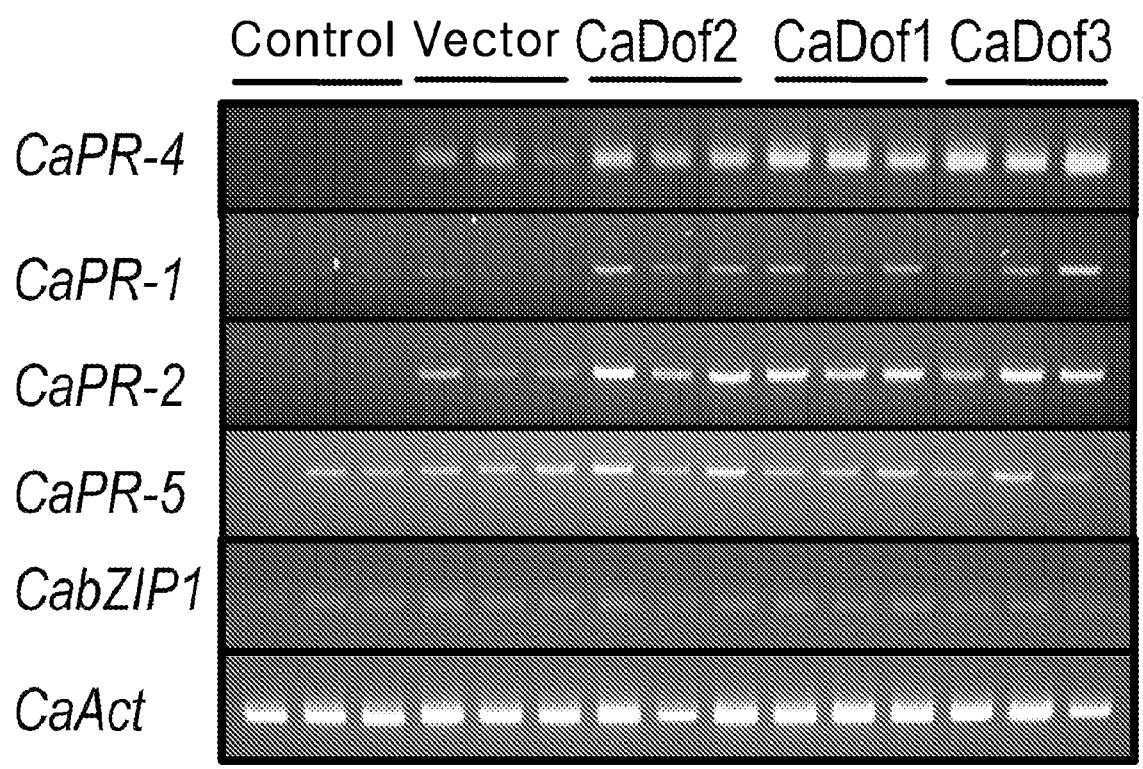

ately used for the regulation of the expression of a target protein in disease-resistant plants.

PROMOTOR OF HOT PEPPER WHICH IS RELATED TO TMV-RESISTANCE

TECHNICAL FIELD

The present invention relates to a promoter of hot pepper related to TMV-resistance, more precisely a promoter of the gene related to TMV-resistance and a method for regulating the expression of a target protein by using a transcription factor binding to the same.

BACKGROUND ART

It is known that the expression of *Capsicum annuum* pathogenesis-related protein 4 (referred as CaPR-4 hereinafter) is increased by TMV infection. However, CaPR-4 gene promoter and TMV-inducible element sequence in pepper have not been identified, yet. Dof1 transcription factor (DNA binding with one finger transcription factor) that binds to the above sequence has not been identified, either.

The TMV-inducible element sequence of the promoter of the gene related to TMV-resistance and Dof1 transcription factor binding to the element sequence can be effectively used for regulating the expression of a target protein in disease-resistant plants.

The present inventors identified the CaPR-4 gene promoter whose expression is increased by TMV infection and the sequence of TMV-inducible element sequence therein. Based on that, the inventors completed this invention by confirming that the element sequence above binds to Dof1 transcription factor and the up-regulation of Dof1 transcription factor results in the up-regulation of CaPR-4, indicating that the promoter of the invention has the function of regulating the expression of a target protein in disease-resistant plants.

DISCLOSURE

Technical Problem

It is an object of the present invention to provide a method for regulating the expression of a target protein in disease-resistant plants.

Technical Solution

To achieve the above object, the present invention provides a polynucleotide having the binding activity to CaDof-1 (*Capsicum annuum* Dof-1; DNA-binding-with one finger) transcription factor containing the nucleic acid sequence represented by SEQ ID NO: 1.

The present invention also provides a gene construct having promoter activity and comprising the minimal promoter operably linked to the above polynucleotide and having the promoter activity induced by TMV infection.

The present invention further provides an expression vector for the expression of a heterologous protein containing the polynucleotide encoding the heterologous protein operably linked to the above gene construct.

The present invention also provides a transgenic plant generated by transforming host cells with the above expression vector.

In addition, the present invention provides a method for regulating the expression of a target protein in host cells comprising the following steps:
1) constructing the expression vector;
2) transforming host cells with the expression vector;
3) culturing the transgenic plant of step 2); and
4) infecting the cultured plant of step 3) with TMV.

ADVANTAGEOUS EFFECT

The method of the present invention can be effectively used for the regulation of the expression of a target protein in disease-resistant plants.

DESCRIPTION OF DRAWINGS

The application of the preferred embodiments of the present invention is best understood with reference to the accompanying drawings, wherein:

FIG. 1 is a diagram showing the Plant cis-acting regulatory DNA elements in CaPR-4 promoter region.

FIG. 2 is a diagram illustrating the reactivities of full length CaPR-4 promoter and deleted promoters with different lengths to the direction of 5'according to the TMV infection.

FIG. 3 is a diagram illustrating the reactivities of full length CaPR-4 promoter and promoter fragments according to the TMV infection.

FIG. 4 is a diagram illustrating the changes of reactivities of TMV-inducible element sequence conjugated to the 35S minimal promoter and promoters with three nucleotide mutations in the above element sequence according to the TMV infection,
PR4-15: CTCTTTAATTTCCCA (SEQ ID NO:2),
PR4-M1: AAATTTAATTTCCCA (SEQ ID NO: 3),
PR4-M2: CTCGGGAATTTCCCA (SEQ ID NO: 6),
PR4-M3: CTCTTTCCCTTCCCA (SEQ ID NO: 7),
PR4-M4: CTCTTTAATGGGCCA (SEQ ID NO: 4), and
PR4-M5: CTCTTTAATTTCTTT (SEQ ID NO: 5).

FIG. 6 is a graph showing the proteins binding to TMV-inducible element sequence of CaPR-4 promoter of nucleoprotein extracted from TMV infected hot pepper, identified by EMSA.

FIG. 7 is a graph illustrating that CaDof1 binds to TMV-inducible element sequence of CaPR-4 promoter.

FIG. 8 is a graph showing the expressions of CaPR-4 and other disease-related genes according to the over-expression of Dofs including CaDof1 in hot pepper plant.

BEST MODE

Figure 5:
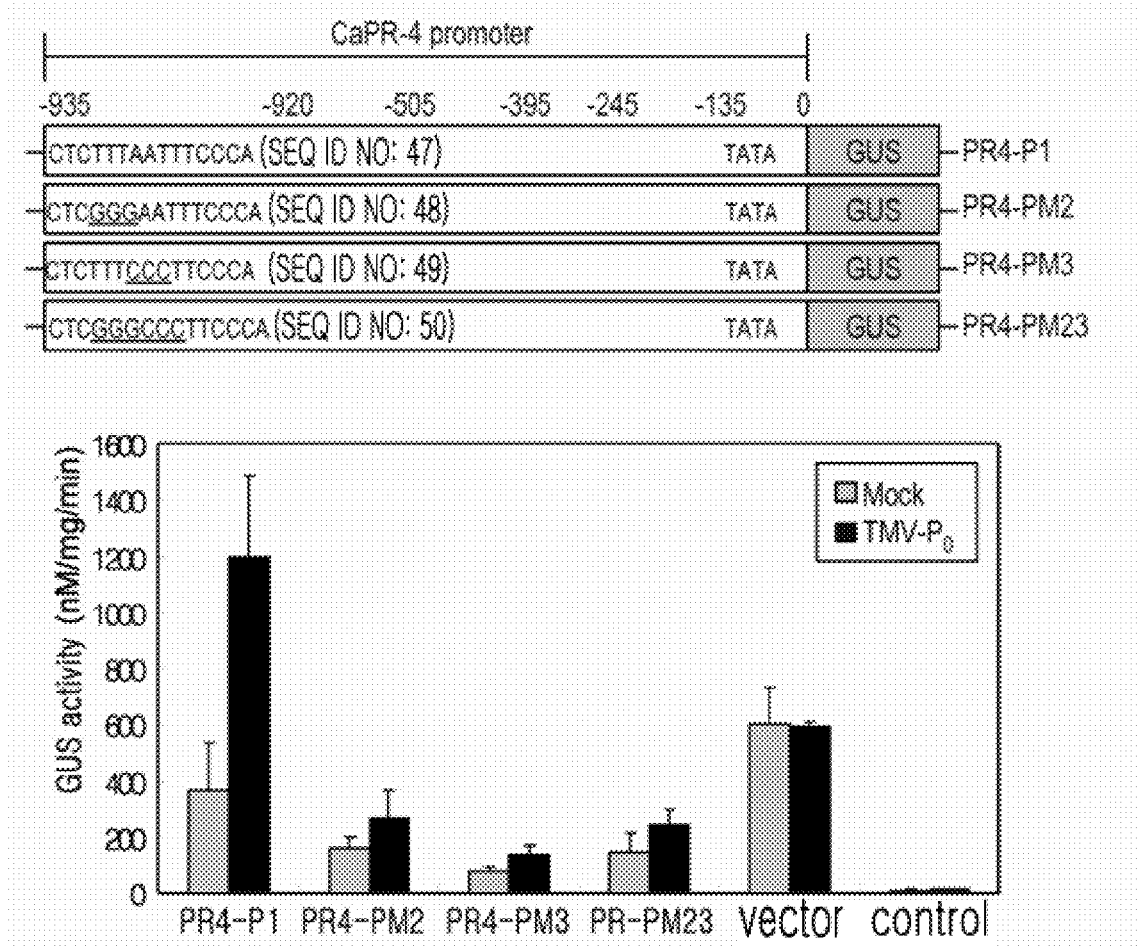
FIG. 5 is a diagram illustrating the changes of reactivities of TMV-inducible element sequence of CaPR-4 promoter and promoters with three nucleotide mutations in the above element sequence according to the TMV infection,
SEQ ID NO: 47 : CTCTTTAATTTCCCA,
SEQ ID NO: 48 : CTCGGGAATTTCCCA,
SEQ ID NO: 49 : CTCTTTCCCTTCCCA, and
SEQ ID NO: 50 : CTCGGGCCCTTCCCA.

Hereinafter, the present invention is described in detail.

The present invention provides a polynucleotide having the binding activity to CaDof-1(*Capsicum annuum* Dof-1; DNA-binding-with one finger) transcription factor containing the nucleic acid sequence represented by SEQ ID NO: 1.

The polynucleotide is characteristically represented by the following formula:

A-X-B

Wherein, A is a polymer of 1-5 nucleic acid molecules or none;
X is TTTAAT (SEQ ID NO: 1); and
B is a polymer of 1-10 nucleic acid molecules or none.

The polynucleotide can be any nucleic acid sequence of those represented by SEQ ID NO: 2-SEQ ID NO: 5:

```
SEQ. ID. NO: 2:     CTCTTTAATTTCCCA;

SEQ. ID. NO: 3:     AAATTTAATTTCCCA;

SEQ. ID. NO: 4:     CTCTTTAATGGGCCA;
and,

SEQ. ID. NO: 5:     CTCTTTAATTTCTTT.
```

As shown in FIG. 1, the present inventors identified CaPR-4 promoter of approximately 935by represented by SEQ ID NO: 8 and confirmed that the promoter is composed of Dof, GT-1 and MYB binding sites in addition to the plant elicitor site such as SA-responsive site or ABA-responsive site.

The deleted promoters cut from 3' to the direction of 5' of the CaPR-4 promoter represented by SEQ ID NO: 8 at 135th, 245th, 395th, 505th, and 585th nucleotides were prepared. Reactivities of the promoters against TMV infection were investigated in the transiently over-expressed plant. As a result, the reactivity of the full length CaPR-4 promoter against TMV was highest (see FIG. 2). Other deleted promoters cut from 3' to the direction of 5' of the CaPR-4promoter represented by SEQ ID NO: 8 at 585th, 840th, 880th, and 920th nucleotides were prepared. Reactivities of the promoters against TMV infection were investigated in the transiently over-expressed hot pepper plant. As a result, reactivity against TMV infection was only detected in the full-length CaPR-4 promoter (see FIG. 3).

Reactivities of the promoter region between −936 and −920 bp from the transcription start site (SEQ ID NO: 2) of the promoter represented by SEQ ID NO: 8 containing the nucleotide sequence comprising Dof transcription factor binding site (see FIG. 1) and mutants (SEQ ID NO: 6 and NO: 7; SEQ ID NO: 6: CTCGGGAATTTCCCA; SEQ ID NO: 7: CTCTTTCCCTTCCCA) thereof against TMV infection were investigated in the transiently over-expressed hot pepper plant. As a result, particularly when CTTT was mutated (PR4-M2) which has been known as Dof transcription factor binding site, the reactivity against TMV infection was hardly detected (see FIG. 4). The promoters partially mutated in the region between −936 and −920 bp from the transcription start site of the promoter represented by SEQ ID NO: 8 were constructed. Reactivities of the mutant promoters and the promoter represented by SEQ ID NO: 1 against TMV infection were investigated in the transiently over-expressed hot pepper plant. As a result, when the transient over-expression was induced by the mutant promoters, the reactivity against TMV infection disappeared (see FIG. 5).

To look for possible candidates that could bind to the TMV-inducible element sequence, EMSA was performed with the hot pepper nuclear proteins. As a result, at least two proteins were confirmed to be bound to the TMV-inducible element sequence (see FIG. 6). And the protein bound to the TMV-inducible element sequence was identified as *Capsicum annuum* Dof1 (CaDof1) (see FIG. 7). The over-expression of CaDof1 affected the expressions of CaPR-4 gene and other disease-related genes. In particular, the CaPR-4 gene expression was increased (see FIG. 8).

The present invention also provides a gene construct having promoter activity and comprising the minimal promoter operably linked to the above polynucleotide and having the promoter activity induced by TMV infection.

The above minimal promoter (CaMV 35S minimal promoter) is the minimal nucleotide involved in gene expression and isolated from cauliflower mosaic virus promoter known that is expressed in plants.

The present invention further provides an expression vector for the expression of a heterologous protein containing the polynucleotide encoding the heterologous protein operably linked to the gene construct of the present invention.

The heterologous protein herein can be any protein that can be mass-produced by those in the art or any protein that is expressed to give specific characteristics to a target transformant. In fact, the heterologous protein includes every protein that is able to be expressed in a transformant by the recombinant expression vector containing the polynucleotide encoding the protein.

The promoter above or TMV-inducible element sequence can be operably linked to the backbone vector in order to be located at the upstream of the target protein. The backbone vector is exemplified by pCAMBIA2300, pBI101, pBI121, etc, but not always limited thereto and any vector that is used for the transformation of a plant can be used.

The present invention also provides a transgenic plant by transforming host cells with the expression vector of the present invention.

The host cell herein is not limited but preferably disease-resistant plant, more preferably TMV-resistant plant, which is exemplified by hot pepper (*Capsicum annuum* L. cv.) Bugang plant, tobacco Samsun NN plant, etc. In a preferred embodiment of the present invention, hot pepper (*Capsicum annuum* L. cv.) Bugang plant was selected as the host cell.

The transformation is the transient over-expression of a heterologous protein in host cells.

In addition, the present invention provides a method for regulating the expression of a target protein comprising the following steps:

1) constructing the expression vector of the present invention;
2) transforming host cells with the expression vector of step 1);
3) culturing the transgenic plant prepared in step 2); and,
4) infecting the cultured plant of step 3) with TMV.

Herein, the expression vector contains the promoter represented by SEQ ID NO: 1 or TMV-inducible element sequence comprising the 1st-15th nucleotides of the promoter or the 3rd-6th nucleotides of the promoter.

The promoter of the invention or TMV-inducible element sequence is activated by the TMV infection of step 4) and then can regulate the expression of a target protein.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Hot Pepper Cultivation and TMV Inoculation

<1-1> Hot Pepper Cultivation

Hot pepper (*Capsicum annuum* L. cv. Bugang Plants; Hungnong Seeds, Korea) was seeded, germinated and cultivated in a 25° C. green house or a plant incubator under the condition of light:dark=16 h:8 h. The Bugang plant showed resistance against TMV pathotype $P_0$ but sensitivity to $P_{1,2}$.

<1-2> TMV Inoculation

TMV was mixed with carborundum (Hayashi Chemical, Japan). The hot pepper plant leaves grown for 2 months were scrubbed with the TMV mixture using a brush to inoculate TMV.

EXAMPLE 2

Construction of Promoter Trap Library

<2-1> Genomic DNA Extraction

Genomic DNA was extracted from the hot pepper cultivated in Example <1-1>.

1 g of the hot pepper leaves was frozen in liquid nitrogen, followed by homogenization. Then it was transferred into a 50 ml tube containing 6 ml urea extract solution [8 M urea, 0.35 M NaCl, 0.05 M Tris-Cl, pH 8.0, 0.02 M EDTA, pH 8.0, 2% N-lauroylsarcosine (Sigma aldrich, USA)]. Same amount of phenol/chloroform/isoamylalcohol mixture was added thereto, which was carefully mixed. The mixture was centrifuged at 8,000 rpm for 10 minutes at room temperature. 1 ml of 4.4 M ammonium acetate (pH 5.2) was added to the supernatant to raise salt concentration. Ethanol was added to the supernatant twice the volume of it to separate DNA. The DNA was dissolved in TE (pH 8.0) fast but carefully.

<2-2> Preparation of Primer

Adaptor-ligated genomic DNA fragments (or called Genome Walker libraries) were prepared by using the genomic DNA extracted from the hot pepper plant in Example <2-1>. Particularly, the genomic DNA of hot pepper was treated with the restriction enzymes such as EcoRV, Dral, Pvull and Sspl, which was linked to adaptor to complete the library. To identify the promoter region of CaPR-4 gene, PCR was performed with the Genome Walker library using gene specific primers (SEQ ID NO: 9: 5'-CACTCGAGCGGCT-TGTCAGCATCCCAAG-3' and SEQ ID NO: 10: 5'-CTTGT-CAGCATCCCAAGTAGCGCAATTAG-3') and adaptor primers (SEQ ID NO: 45: 5'-GTAATACGACTCACTAT-AGGGC-3' and SEQ ID NO: 46: 5'-ACTAT-AGGGCACGCGTGGT-3') as follows: 94° C./5 minutes, 72° C./3 minutes (7 cycles), 94° C./25 seconds, 67° C./3 minutes (32 cycles) and 67° C./7 minutes.

<2-3> Analysis of Cis-Acting Regulatory Elements

Analysis of the sequences of the promoter represented by SEQ ID NO: 1 identified by the method of Example <2-2> using Web Signal Scan Program: PLACE (//www.dna.affrc.go.jp/PLACE/) and PlantCARE (//bioinformatics.psb.ugent.be/webtools/plantcare/html/) was performed.

As a result, as shown in FIG. 1, the region of CaPR-4 promoter in a 935 bp sequence represented by SEQ ID NO: 1 was obtained. The sequence contained Dof, GT-1 and MYB binding sites in addition to the plant elicitor site such as SA-responsive site or ABA-responsive site.

EXAMPLE 3

Reactivity of the Deleted Promoter

<3-1> Transformant Transformed with the Vector Containing the Deleted Promoter

Deleted promoters were prepared by cutting at 135th, 245th, 395th, 505th and 585th nucleotide from 3' to the direction of 5' of the promoter sequence represented by SEQ ID NO: 1. The deleted promoters and the full length promoter represented by SEQ ID NO: 1 were introduced into the upstream of GUS gene of pCAMBIA1305.2 vector (CAMBIA Bio Forge, USA). The vector was transiently over-expressed in the hot pepper plant cultivated in Example <1-1>.

Particularly, the deleted promoters were amplified by PCR using the genomic DNA extracted from the hot pepper plant by the same manner as described in Example <2-1> with the primers (sense: SEQ ID NO: 11: 5'-GGATCCCTCTT-TAATTTCCCAAAC-3', SEQ ID NO: 12: 5'-GGATC-CTATATTAGTTAATAAAGA-3', SEQ ID NO: 13: 5'-GGATCCAATTAAAAATATGTCTTC-3', SEQ ID NO: 14: 5'-GGATCCGCTCCATACTATACG-3', SEQ ID NO: 15: 5'-GGATCCAAGGACTAGTTATGTTTT-3', SEQ ID NO: 16: 5'-GGATCCTAGAATAGTAAGACGAAA-3'; antisense: SEQ ID NO: 17: 5'-CCATGGCATGATATTGTAATTGTA-3') having the nucleotide sequences of BamH1 (sense) and Nco1 (antisense) restriction enzyme recognition sites as follows: 94° C./5 minutes, 72° C./3 minutes (7 cycles), 94° C./25 seconds, 67° C./3 minutes (32 cycles) and 67° C./7 minutes. The amplified promoter was inserted into pGEM-T easy vector (Promega, USA), which was digested with the above restriction enzymes. The deleted promoters were introduced into the upstream of GUS gene of pCAMBIA1305.2 vector treated with BamH1 and Nco1. Each deleted CaPR-4 promoter was introduced into Agrobacterium EHA105 (Accession No: KCTC 10855BP). The Agrobacterium EHA105 cells containing the promoters were injected into the leaves of four- to six-week-old tobacco plant at an OD600 of 1.0. After 3 days, the infiltrated leaves were cut and used for the measurement of GUS activity.

<3-2> Reactivity Against TMV Infection

The transgenic plant prepared in Example <3-1> was treated with TMV by the same manner as described in Example <1-2>, followed by measuring the GUS activity.

Particularly, proteins were extracted with CCLR buffer [100 mM potassium phosphate (pH 7.8), 1 mM EDTA, 7 mM 2-mercaptoethanol, 1% (v/v) Triton X-100, 10% (v/v) glycerol; Sigma Aldrich, USA] from the tobacco leaves infected with TMV. The extracted protein was mixed with GUS buffer 1 [1×CCLR buffer containing 2 mM 4-methylumbelliferyl β-D-glycyronide (MUG; Sigma Aldrich, USA)], followed by reaction at 37° C. for one hour. The reaction was terminated by adding the stop buffer (0.2M $Na_2CO_3$). The samples were read in emission of 455 nm when the excitation was 365 nm using a fluorimeter (Mithras LB 940, Berthold, USA).

As a result, as shown in FIG. 2, the full length CaPR-4 promoter showed the highest reactivity against TMV infection.

EXAMPLE 4

Reactivity of the Deleted Promoter 2

<4-1> Transformant Transformed with the Vector Containing the Deleted Promoter

The deleted promoters cut at 585th, 840th, 880th, and 920th nucleotide from 3' to the direction of 5' of the promoter sequence represented by SEQ ID NO: 1 were amplified by PCR using the genomic DNA extracted from the hot pepper plant by the same manner as described in Example <2-1> with the primers (sense: SEQ ID NO: 18: 5'-GGATCCA-CAAAATTGAGTATCATA-3' SEQ ID NO: 19: 5'-GGATC-CTGAAATTGACCCCCAGCT-3' SEQ ID NO: 20: 5'-GGATCCATACTATACTACGTATAA-3', SEQ ID NO: 16; antisense: SEQ ID NO: 17) having the nucleotide sequences of BamH1 (sense) and Nco1 (antisense) restriction enzyme recognition sites as follows: 95° C./5 minutes, 95° C./30 seconds, 55° C./20 seconds, 72° C./30 seconds, 24 cycles, and 72° C./10 minutes. The deleted promoters and the promoter represented by SEQ ID NO: 1 were introduced into the upstream of GUS gene of pCAMBIA1305.2 vector by the same manner as described in Example <3-1>. The hot pepper plant cultivated in Example <1-1> was transformed with the vector.

<4-2> Reactivity Against TMV Infection

The transgenic plant prepared by the same manner as descried in Example <4-1> was treated with TMV by the same manner as described in Example <1-2>. GUS activity was measured by the same manner as described in Example <3-2>.

As a result, as shown in FIG. 3, reactivity against TMV infection was only detected in the full length CaPR-4 promoter.

EXAMPLE 5

Reactivity of the Deleted Promoter 3

<5-1> Transformant Transformed with the Vector Containing the Deleted Promoter

Deleted promoter having a sequence between −936 and −920 bp from the transcription start site of the promoter represented by SEQ ID NO: 1 and confirmed to have the nucleotide sequence of Dof transcription factor binding site in Example 2 and mutants thereof were prepared and introduced into the upstream of 35S minimal promoter which was inserted by using EcoR1 and Nco1 in the vector pCAMBIA 1305.2 where 35S promoter was eliminated. This modified vector was transiently over-expressed in the tobacco plant cultivated by the same manner as described in Example <1-1>. The 35S promoter included in pCAMBIA1305.2 vector was eliminated by using EcoRI and NcoI, to which 35S minimal promoter oligomer (Bioneer, Korea) was inserted by using ligase.

Particularly, the mutant promoters were amplified by PCR using the genomic DNA extracted from the hot pepper plant by the same manner as described in Example <2-1> with the sense primers (SEQ ID NO: 21: 5'-GGATCCAAATT-TAATTTCCCAAAC-3', SEQ ID NO: 22: 5'-GGATC-CCTCGGGAATTTCCCAAAC-3', SEQ ID NO: 23: 5'-GGATCCCTCTTTCCCTTCCCAAAC-3', SEQ ID NO: 24: 5'-GGATCCCTCTTAATGGGCCAAAC-3', SEQ ID NO: 25: 5'-GGATCCCTCTTTAATTTCTTTAAC-3') containing the nucleotide sequence of BamH1 and the antisense primer (SEQ ID NO: 17) as follows: 95° C./5 minutes, 95° C./30 seconds, 55° C./20 seconds, 72° C./30 seconds, 24 cycles, and 72° C./10 minutes. The amplified promoter was inserted into pGEM-T easy vector, which was digested with the above restriction enzymes. The promoter fragments were introduced into the upstream of GUS gene of pCAM-BIA1305.2 vector treated with BamH1 and Nco1.

<5-2> Reactivity Against TMV Infection

The transgenic plant prepared by the same manner as descried in Example <5-1> was treated with TMV by the same manner as described in Example <1-2>. GUS activity was measured by the same manner as described in Example <3-2>.

As a result, as shown in FIG. 4, reactivity against TMV infection was almost gone when CTTT, known as D of transcription factor binding site, was mutated (PR4-M2).

EXAMPLE 6

Reactivity of the Deleted Promoter 3

<6-1> Transformant Transformed with the Vector Containing the Deleted Promoter

PR4-PM23 having a partially mutated sequence between −936 and −920 bp from the transcription start site of the promoter represented by SEQ ID NO: 1 was prepared and introduced into the upstream of GUS gene of pCAMBIA 1305.2 vector. This modified vector was transiently over-expressed in the tobacco plant cultivated by the same manner as described in Example <1-1>.

The PR4-PM23 promoter was obtained by the same manner as described in Example <5-1> by PCR with the sense primer (SEQ ID NO: 26: 5'-GGATCCCTCGGGCCCTTC-CCAAAC-3') containing the nucleotide sequence of BamH1 and the antisense primer represented by SEQ ID NO: 17.

<6-2> Reactivity Against TMV Infection

The transgenic plant prepared by the same manner as descried in Example <6-1> was treated with TMV by the same manner as described in Example <1-2>. GUS activity was measured by the same manner as described in Example <3-2>.

As a result, as shown in FIG. 5, reactivity against TMV infection was almost gone when the plant was transformed with the deleted promoter, but not when transformed with wild type promoter.

EXAMPLE 7

Identification of Transcription Factor Binding to TMV-Inducible Element Sequence by EMSA <7-1> Construction of Probe and Primer for EMSA Oligomers represented by SEQ ID NO: 27 (5'-CTCTT-TAATTTCCCA-3') and SEQ ID NO: 28 ('3-TGGGAAAT-TAAAGAG-3') were prepared and reacted at 94° C. for one minute, followed by ligation for 16 hours. The ligated oligomer was added into 32P-CTP labeling solution (3 mM dATP, dGTP, dTTP, 10× Klenow enzyme buffer, Klenow enzyme, 32P-CTP; Perkin Elmer, USA) and reacted for 30 minutes at room temperature to prepare the probe for EMSA.

<7-2> Sample

The nuclear proteins were extracted from the hot pepper plant cultivated in Example 1.

Particularly, 10 g of the frozen leaves was homogenized in 250 ml of nucleus isolation buffer [40% (w/v) glycerol, 600 mM sucrose, 25 mM Tris (pH 8.0), 5 mM $MgCl_2$, 2 mM spermine, 10 mM β-mercaptoethanol, 1 mM protease inhibitor (PI); Sigma Aldrich, USA]. The suspension was filtered through Miracloth (Calbiochem, Germany) and stirred for 15 min after addition of 0.6% Nonidet P-40 (Sigma, USA). The slurry was centrifuged for 10 min at 5,000 rpm. The pellets were resuspended in 15 ml of mannitol buffer [250 mM mannitol, 25 mM Tris (pH 8.0), 5 mM $MgCl_2$, 10 mM β-mercaptoethanol, 1 mM PI] and layered with 95% (w/v) Percol (Amersham Biosciences, Sweden) in the mannitol buffer; followed by centrifugation for 10 min at 5,000 g. After layering with 75% (w/v) Percol again, pellets were obtained by centrifugation at 5,000 rpm for 10 min. From the pellets containing nuclei, the nuclear proteins were extracted by using the protein extraction solution (50 mM Tris-HCl, pH 8, 10 mM EDTA, 1% SDS, 1 mM PMSF; Sigma Aldrich, USA).

<7-3> EMSA

1 μl of the probe (2 μM) for EMSA prepared in Example <7-1>, 2 μg of the hot pepper nuclear protein obtained in Example <7-2>, 4×reaction buffer [200 mM KCl, 100 mM HEPES/KOH(pH 7.9), 2 mM DTT, 20% glycerol, 20 μg/μl BSA], 1 μg of poly dIdC (Pharmacia, USA) mixture and 1 μl of 1% (w/v) Nonidet P40 were mixed. After incubation for 30 min at root temperature, 10 μl of the reaction mixture was loaded on a 6% non-denatured polyacrylamide gel. Electrophoresis was performed in 0.5×TBE (54 mM Tris-borate, pH 8.3, 1 mM EDTA) for 2.5 h. Gels were dried and exposed for autoradiography using X-ray film (Fuji, Japan).

As a result, as shown in FIG. 6, at least two of hot pepper nuclear proteins were bound to TMV-inducible element sequence.

EXAMPLE 8

Binding of Hot Pepper Dof1 to TMV-inducible Element Sequence

<8-1> CaDof1 Obtainment

Total RNA was extracted from the hot pepper cultivated in Example <1-1>, followed by RT-PCR to obtain cDNA.

Particularly, 1 g of plant tissue was frozen in liquid nitrogen and homogenized, to which 10 ml of RNA extraction buffer (0.2 M Tris-Cl, pH 8.0, 0.4 M $LiCl_2$, 25 mM EDTA, pH 8.0 and 1% SDS) was added. After adding 10 ml of aquaphenol, the mixture was well mixed and centrifuged at 4° C., 10,000 g, for 20 minutes. The supernatant was transferred into a tube containing 10 ml of chloroform and well mixed, followed by centrifugation at 4° C., 10,000 g, for 20 minutes. RNA in the supernatant was precipitated by using ethanol. The precipitate containing RNA was washed with 75% ethanol and dissolved in 2 M $LiCl_2$. RNA was precipitated again and dissolved in DEPC treated water. RT-PCR was performed using 1 mg of the RNA as a template with oligo dT primer (Promega, USA) and reverse transcriptase (Promega, USA) to synthesize cDNA as follows: 72° C./10 minutes and 42° C./1.5 hours.

PCR was performed using the cDNA obtained above as a template with the primers (SEQ ID NO: 29: 5'-GAGCT-CATGGATCCCTCTAGTGCAC-3'; SEQ ID NO: 30: 5'-GAGCTCCATGAGAGGACTATTGTG-3') able to amplify CaDof1 gene represented by SEQ ID. NO: 2 as follows; 95° C./5 minutes, 95° C./30 seconds, 55° C./20 seconds, 72° C./30 seconds, 24 cycles, and 72° C./10 minutes. The PCR product was digested with BamH1 and introduced into pQE30 vector (Qiagen, Germany) to obtain CaDof1 recombinant protein having 6 His tags.

The resulting vector was transformed into *Escherichia coli* strain BL21 (DE3) (Qiagen, Germany). The CaDof1 protein having 6 His tags was over-expressed by 1 mM isopropyl-β-D-thiogalactoside (IPTG). The IPTG-induced *E. coli* transformants were collected and suspended using lysis buffer (50 mM $Na_2HPO_4$, pH 8.0, 300 mM NaCl), and subjected to sonication on ice for 1 min with a Vibracell sonifier (Sonics and Materials, USA). After the resulting lysate was centrifuged for 10 min at 13,000×g, the supernatant was loaded on a Ni-NTA affinity resin (Qiagen, Germany). The CaDof1 recombinant protein was purified by using an eluting solution (50 mM $Na_2HPO_4$, 300 mM NaCl, 10% glycerol).
8-2> EMSA The CaDof1 obtained in Example <8-1> was confirmed to be bound to TMV-inducible element sequence of the promoter represented by SEQ ID NO: 1.

EMSA was performed with 1 μl of the probe for EMSA (2 μM) prepared in Example <7-1> and 100 ng of the CaDof1 recombinant protein obtained in Example <8-1> by the same manner as described in Example <7-3>.

As a result, as shown in FIG. 7, the CaDof1 was confirmed to be bound to TMV-inducible element sequence of the promoter represented by SEQ ID NO: 1.

EXAMPLE 9

Relation of CaDof1 and CaPR-4

<9-1> Construction of the Vector for CaDof1 Over-expression

PCR was performed using the cDNA obtained in Example <8-1> as a template with the primers represented by SEQ ID NO: 31 and NO: 32 (SEQ ID NO: 31: 5'-GAGCTCATG-GATCCCTCTAGTGCAC-3', SEQ ID NO: 32: 5'-GAGCTC-CATGAGAGGACTATTGTG-3') by the same manner as described in Example <8-1>. The PCR product was digested with BamH1 and then introduced into pCAMBIA2300 (CAMBIA Bio Forge, USA).
<9-2> Generation of the Transformant for CaDof1 Over-Expression The vector constructed in Example <9-1> was transiently over-expressed in the hot pepper plant cultivated in Example <1-1> by the same manner as described in Example <3-1>.
<9-3> Relation of CaDof1 and CaPR-4

Genomic DNA was extracted from the transformant prepared in Example <9-2> by the same manner as described in Example <2-1>. PCR was performed using the genomic DNA as a template with the primer sets (SEQ ID NO: 33: 5'-GACATGGGACAATAGGCTAGCAGCC-3' and SEQ ID NO: 34: 5'-CAGTTGGAAGTTCCAATTTGGAATC-3', SEQ ID NO: 35: 5'-ACTCTTTTCCACCATCA-CAGGGTTC-3' and SEQ ID NO: 36: 5'-GTTGAGGTTG-CATTATTATTTTCAG-3', SEQ ID NO: 37: 5'-CGGCGCA-GAGTGCTACGAACGTGAG-3' and SEQ ID NO: 38: 5'-GTCATTGCAGTTGACAAATTCATAG-3', SEQ ID NO: 39: 5'-TGGTGCTGGTAGAGGTTGGTGCCAG-3' and SEQ ID NO: 40: 5'-CTTCATGTGTACTTGTAGGCAACTC-3') for detecting the expressions of CaPR-4, 1, 2 and 5 or the primer sets (SEQ ID NO: 41: AGATCTAATGGATC-CCTCTAGTGCAC and SEQ ID NO: 42: AGATCTCAT-GAGAGGACTATTGAG, SEQ ID NO: 43: GGATC-CCAATGGATACTTCTTCAGTG and SEQ ID NO: 44: GGATCCCCAGGATGATCCTCCTC) for detecting the expressions of CaDof2 and 3 as follows: 95° C./5 minutes, 95° C./30 seconds, 55° C./20 seconds, 72° C./30 seconds, 27 cycles, and 72° C./10 minutes or 95° C./5 minutes, 95° C/30 seconds, 55° C./20 seconds, 72° C./30 seconds, 24 cycles, and 72° C./10 minutes.

As a result, as shown in FIG. 8, the CaDof1 over-expression changed the expressions of other disease-related genes including CaPR-4.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A polynucleotide construct having promoter activity and comprising a minimal promoter operably linked to a polynucleotide having binding activity to CaDof-1 (*Capsicum annuum* DNA binding with one finger) transcription factor and comprising the nucleic acid sequence represented by SEQ ID NO: 1, wherein promoter activity is induced by Tobacco Mosaic Virus (TMV) infection.

2. A nucleic acid for expression of a heterologous protein, wherein the nucleic acid comprises a DNA sequence encoding the heterologous protein operably linked to the polynucleotide construct of claim 1.

3. An expression vector for expression of a heterologous protein comprisinq the nucleic acid of claim 2.

4. A transgenic plant host cell comprisinq the nucleic acid of claim 2.

5. A transgenic plant comprising the nucleic acid of claim 2.

6. The transgenic plant host cell according to claim 4, wherein the heterologous protein is transiently over-expressed.

7. A method for regulating expression of a heterologous protein in transgenic plant host cells comprising the following steps:
 1) constructing the expression vector of claim 3;
 2) transforming plant host cells with the expression vector of claim 5 to produce transgenic plant host cells;
 3) culturing the transgenic plant host cells of step 2), said transgenic plant host cells comprising the nucleic acid which comprises a DNA sequence encoding the heterologous protein operably linked to the polynucleotide construct, said polynucleotide construct having promoter activity and comprising the minimal promoter operably linked to a polynucleotide having binding activity to the CaDof-1 transcription factor and comprising the nucleic acid sequence of SEQ ID NO: 1, wherein promoter activity is induced by Tobacco Mosaic Virus (TMV) infection; and
 4) infecting the cultured transgenic plant host cells of step 3) with TMV.

\* \* \* \* \*

SEQUENCE LISTING

<160> NUMBER OF SEQ ID NOS: 50

<210> SEQ ID NO 1
<211> LENGTH: 6
<212> TYPE: DNA
<213> ORGANISM: Artificial Sequence

```
<220> FEATURE:
<223> OTHER INFORMATION: Synthetic construct: oligonucleotide sequence
      x.

<400> SEQUENCE: 1 tttaat                                                                    6

<210> SEQ ID NO 2
<211> LENGTH: 15
<212> TYPE: DNA
<213> ORGANISM: Artificial Sequence
<220> FEATURE:
<223> OTHER INFORMATION: Synthetic construct: oliognucleotide PR4-15.

<400> SEQUENCE: 2
ctctttaatt tccca                                                         15

<210> SEQ ID NO 3
<211> LENGTH: 15
<212> TYPE: DNA
<213> ORGANISM: Artificial Sequence
<220> FEATURE:
<223> OTHER INFORMATION: Synthetic construct: oliognucleotide PR4-M1.

<400> SEQUENCE: 3
aaatttaatt tccca                                                         15

<210> SEQ ID NO 4
<211> LENGTH: 15
<212> TYPE: DNA
<213> ORGANISM: Artificial Sequence
<220> FEATURE:
<223> OTHER INFORMATION: Synthetic construct: oligonucleotide PR4-M4.

<400> SEQUENCE: 4
ctctttaatg ggcca                                                         15

<210> SEQ ID NO 5
<211> LENGTH: 15
<212> TYPE: DNA
<213> ORGANISM: Artificial Sequence
<220> FEATURE:
<223> OTHER INFORMATION: Synthetic construct: oligonucleotide PR4-M5.

<400> SEQUENCE: 5
ctctttaatt tcttt                                                         15

<210> SEQ ID NO 6
<211> LENGTH: 15
<212> TYPE: DNA
<213> ORGANISM: Artificial Sequence
<220> FEATURE:
<223> OTHER INFORMATION: Synthetic construct: oligonucleotide PR4-M2.

<400> SEQUENCE: 6
ctcgggaatt tccca                                                         15

<210> SEQ ID NO 7
<211> LENGTH: 15
<212> TYPE: DNA
<213> ORGANISM: Artificial Sequence
<220> FEATURE:
<223> OTHER INFORMATION: Synthetic construct: oligonucleotide PR4-M3.

<400> SEQUENCE: 7
ctctttccct tccca                                                         15
```

```
<210> SEQ ID NO 8
<211> LENGTH: 935
<212> TYPE: DNA
<213> ORGANISM: Artificial Sequence
<220> FEATURE:
<223> OTHER INFORMATION: Synthetic construct: CaPR-4 PROMOTER sequence.

<400> SEQUENCE: 8
ctctttaatt tcccaaacga aatagcctct tagcttgttt atctacacgt actggagaag      60
actattcttc agcataaatg gtcaaattaa gcaacagttt taatttgtcc agtgttttta     120 aagcttttt cgaacgagtt ttagggcggg gcgtataaaa aatgttctat actgtaaata     180
aaaagtgtag attcatagga aataaaagtg tacgtccccg acgtcagctt attttacta     240 tgttaaaagt ttttttgcta ccgatcatat ttttattatt ggtttaatga cagttaagat     300
ttatgctatc atattttctt attgtaattt gtagctattc ttttctaaa tatattagtt     360 aataaagaaa acaattttcg taaaaaataa ttataatatt ttatttctat attaatggga     420
tttatgggat aattaaaaat atgtcttctt cttattaaca aaattacaaa attgagtatc     480
atatgatata cacccaataa attcatgaaa ttgaccccca cgtttgaaaa cttacgcctc     540
gctccatact atactacgta taatgccttg cctcatgacc ctgccttta aaggactagt     600 tatgttttgt ctatgctcta cctctagata acatcaacat ttgacaaatc aatatggtag     660
ctagctgact aattacgtag taagttaaat catcagaatt tagaatagta agacgaaaag     720
attgaagaat tttcctacaa ggagtttgag agagttccag tctttcacaa ctacatgaga     780
aattaataac aacaatgact tttcaaagtc atcaagcgca ccgcatgtcc attaatttcc     840
acactaatta ctagctagtt tacctataaa taaggcctat ttatccttca ccatttcacg     900
gaaatcccac aagaaattac aattacaata tcatg                                 935

<210> SEQ ID NO 9
<211> LENGTH: 28
<212> TYPE: DNA
<213> ORGANISM: Artificial Sequence
<220> FEATURE:
<223> OTHER INFORMATION: Synthetic construct: CaPR-4 PROMOTER forward
      primer.

<400> SEQUENCE: 9
cactcgagcg gcttgtcagc atcccaag                                          28

<210> SEQ ID NO 10
<211> LENGTH: 29
<212> TYPE: DNA
<213> ORGANISM: Artificial Sequence
<220> FEATURE:
<223> OTHER INFORMATION: Synthetic construct: CaPR-4 PROMOTER reverse
      primer.

<400> SEQUENCE: 10
cttgtcagca tcccaagtag cgcaattag                                         29

<210> SEQ ID NO 11
<211> LENGTH: 24
<212> TYPE: DNA
<213> ORGANISM: Artificial Sequence
<220> FEATURE:
<223> OTHER INFORMATION: Synthetic construct: PR4-P1 sense primer.

<400> SEQUENCE: 11
ggatccctct ttaatttccc aaac                                              24
```

```
<210> SEQ ID NO 12
<211> LENGTH: 24
<212> TYPE: DNA
<213> ORGANISM: Artificial Sequence
<220> FEATURE:
<223> OTHER INFORMATION: Synthetic construct:  PR4-P2 sense primer.

<400> SEQUENCE: 12
ggatcctata ttagttaata aaga                                         24

<210> SEQ ID NO 13
<211> LENGTH: 24
<212> TYPE: DNA
<213> ORGANISM: Artificial Sequence
<220> FEATURE:
<223> OTHER INFORMATION: Synthetic construct:  PR4-P3 sense primer.

<400> SEQUENCE: 13
ggatccaatt aaaaatatgt cttc                                         24

<210> SEQ ID NO 14
<211> LENGTH: 21
<212> TYPE: DNA
<213> ORGANISM: Artificial Sequence
<220> FEATURE:
<223> OTHER INFORMATION: Synthetic construct:  PR4-P4 sense primer.

<400> SEQUENCE: 14
ggatccgctc catactatac g                                            21

<210> SEQ ID NO 15
<211> LENGTH: 24
<212> TYPE: DNA
<213> ORGANISM: Artificial Sequence
<220> FEATURE:
<223> OTHER INFORMATION: PR4-P5 sense primer

<400> SEQUENCE: 15
ggatccaagg actagttatg tttt                                         24

<210> SEQ ID NO 16
<211> LENGTH: 24
<212> TYPE: DNA
<213> ORGANISM: Artificial Sequence
<220> FEATURE:
<223> OTHER INFORMATION: Synthetic construct:  PR4-P6 sense primer.

<400> SEQUENCE: 16
ggatcctaga atagtaagac gaaa                                         24

<210> SEQ ID NO 17
<211> LENGTH: 24
<212> TYPE: DNA
<213> ORGANISM: Artificial Sequence
<220> FEATURE:
<223> OTHER INFORMATION: Synthetic construct:  antisense primer.

<400> SEQUENCE: 17
ccatggcatg atattgtaat tgta                                         24

<210> SEQ ID NO 18
<211> LENGTH: 24
<212> TYPE: DNA
<213> ORGANISM: Artificial Sequence
<220> FEATURE:
<223> OTHER INFORMATION: Synthetic construct:  PR4-P1-1 sense primer.
```

-continued

<400> SEQUENCE: 18
ggatccacaa aattgagtat cata                                              24

<210> SEQ ID NO 19
<211> LENGTH: 24
<212> TYPE: DNA
<213> ORGANISM: Artificial Sequence
<220> FEATURE:
<223> OTHER INFORMATION: Synthetic construct: PR4-P1-2 sense primer.

<400> SEQUENCE: 19
ggatcctgaa attgacccccc agct                                             24

<210> SEQ ID NO 20
<211> LENGTH: 24
<212> TYPE: DNA
<213> ORGANISM: Artificial Sequence
<220> FEATURE:
<223> OTHER INFORMATION: Synthetic construct: PR4-P1-3 sense primer.

<400> SEQUENCE: 20
ggatccatac tatactacgt ataa                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic construct: PR4-M1 sense primer.

<400> SEQUENCE: 21
ggatccaaat ttaatttccc aaac                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic construct: PR4-M2 sense primer.

<400> SEQUENCE: 22
ggatccctcg ggaatttccc aaac                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic construct: PR4-M3 sense primer.

<400> SEQUENCE: 23
ggatccctct ttcccttccc aaac                                              24

<210> SEQ ID NO 24
<211> LENGTH: 23
<212> TYPE: DNA
<213> ORGANISM: Artificial Sequence
<220> FEATURE:
<223> OTHER INFORMATION: Synthetic construct: PR4-M4 sense primer.

<400> SEQUENCE: 24
ggatccctct taatgggcca aac                                               23

-continued

```
<210> SEQ ID NO 25
<211> LENGTH: 24
<212> TYPE: DNA
<213> ORGANISM: Artificial Sequence
<220> FEATURE:
<223> OTHER INFORMATION: Synthetic construct: PR4-M5 sense primer.

<400> SEQUENCE: 25
ggatccctct ttaatttctt taac                                          24

<210> SEQ ID NO 26
<211> LENGTH: 24
<212> TYPE: DNA
<213> ORGANISM: Artificial Sequence
<220> FEATURE:
<223> OTHER INFORMATION: Synthetic construct: PR4-PM23 sense primer.

<400> SEQUENCE: 26
ggatccctcg ggcccttccc aaac                                          24

<210> SEQ ID NO 27
<211> LENGTH: 15
<212> TYPE: DNA
<213> ORGANISM: Artificial Sequence
<220> FEATURE:
<223> OTHER INFORMATION: Synthetic construct: EMSA probe 1.

<400> SEQUENCE: 27
ctctttaatt tccca                                                    15

<210> SEQ ID NO 28
<211> LENGTH: 15
<212> TYPE: DNA
<213> ORGANISM: Artificial Sequence
<220> FEATURE:
<223> OTHER INFORMATION: Synthetic construct: EMSA probe 2.

<400> SEQUENCE: 28
tgggaaatta aagag                                                    15

<210> SEQ ID NO 29
<211> LENGTH: 25
<212> TYPE: DNA
<213> ORGANISM: Artificial Sequence
<220> FEATURE:
<223> OTHER INFORMATION: Synthetic construct: CaDof1 forward primer 1.

<400> SEQUENCE: 29
gagctcatgg atccctctag tgcac                                         25

<210> SEQ ID NO 30
<211> LENGTH: 24
<212> TYPE: DNA
<213> ORGANISM: Artificial Sequence
<220> FEATURE:
<223> OTHER INFORMATION: Synthetic construct: CaDof1 reverse primer 1.

<400> SEQUENCE: 30
gagctccatg agaggactat tgtg                                          24

<210> SEQ ID NO 31
<211> LENGTH: 25
<212> TYPE: DNA
<213> ORGANISM: Artificial Sequence
<220> FEATURE:
<223> OTHER INFORMATION: Synthetic construct: CaDof1 forward primer 2.
```

```
<400> SEQUENCE: 31
gagctcatgg atccctctag tgcac                                      25

<210> SEQ ID NO 32
<211> LENGTH: 24
<212> TYPE: DNA
<213> ORGANISM: Artificial Sequence
<220> FEATURE:
<223> OTHER INFORMATION: Synthetic construct: CaDof1 reverse primer 2.

<400> SEQUENCE: 32
gagctccatg agaggactat tgtg                                       24

<210> SEQ ID NO 33
<211> LENGTH: 25
<212> TYPE: DNA
<213> ORGANISM: Artificial Sequence
<220> FEATURE:
<223> OTHER INFORMATION: Synthetic construct: CaPR-4 forward primer.

<400> SEQUENCE: 33
gacatgggac aataggctag cagcc                                      25

<210> SEQ ID NO 34
<211> LENGTH: 25
<212> TYPE: DNA
<213> ORGANISM: Artificial Sequence
<220> FEATURE:
<223> OTHER INFORMATION: Synthetic construct: CaPR-4 reverse primer.

<400> SEQUENCE: 34
cagttggaag ttccaatttg gaatc                                      25

<210> SEQ ID NO 35
<211> LENGTH: 25
<212> TYPE: DNA
<213> ORGANISM: Artificial Sequence
<220> FEATURE:
<223> OTHER INFORMATION: Synthetic construct: CaPR-1 forward primer.

<400> SEQUENCE: 35
actcttttcc accatcacag ggttc                                      25

<210> SEQ ID NO 36
<211> LENGTH: 25
<212> TYPE: DNA
<213> ORGANISM: Artificial Sequence
<220> FEATURE:
<223> OTHER INFORMATION: Synthetic construct: CaPR-1 reverse primer.

<400> SEQUENCE: 36
gttgaggttg cattattatt ttcag                                      25

<210> SEQ ID NO 37
<211> LENGTH: 25
<212> TYPE: DNA
<213> ORGANISM: Artificial Sequence
<220> FEATURE:
<223> OTHER INFORMATION: Synthetic construct: CaPR-2 forward primer.

<400> SEQUENCE: 37
cggcgcagag tgctacgaac gtgag                                      25
```

```
<210> SEQ ID NO 38
<211> LENGTH: 25
<212> TYPE: DNA
<213> ORGANISM: Artificial Sequence
<220> FEATURE:
<223> OTHER INFORMATION: Synthetic construct: CaPR-2 reverse primer.

<400> SEQUENCE: 38
gtcattgcag ttgacaaatt catag                                          25

<210> SEQ ID NO 39
<211> LENGTH: 25
<212> TYPE: DNA
<213> ORGANISM: Artificial Sequence
<220> FEATURE:
<223> OTHER INFORMATION: Synthetic construct: CaPR-5 forward primer.

<400> SEQUENCE: 39
tggtgctggt agaggttggt gccag                                          25

<210> SEQ ID NO 40
<211> LENGTH: 25
<212> TYPE: DNA
<213> ORGANISM: Artificial Sequence
<220> FEATURE:
<223> OTHER INFORMATION: Synthetic construct: CaPR-5 reverse primer.

<400> SEQUENCE: 40
cttcatgtgt acttgtaggc aactc                                          25

<210> SEQ ID NO 41
<211> LENGTH: 26
<212> TYPE: DNA
<213> ORGANISM: Artificial Sequence
<220> FEATURE:
<223> OTHER INFORMATION: Synthetic construct: CaDof2 forward primer.

<400> SEQUENCE: 41
agatctaatg gatccctcta gtgcac                                         26

<210> SEQ ID NO 42
<211> LENGTH: 24
<212> TYPE: DNA
<213> ORGANISM: Artificial Sequence
<220> FEATURE:
<223> OTHER INFORMATION: Synthetic construct: CaDof2 reverse primer.

<400> SEQUENCE: 42
agatctcatg agaggactat tgag                                           24

<210> SEQ ID NO 43
<211> LENGTH: 26
<212> TYPE: DNA
<213> ORGANISM: Artificial Sequence
<220> FEATURE:
<223> OTHER INFORMATION: Synthetic construct: CaDof3 forward primer.

<400> SEQUENCE: 43
ggatcccaat ggatacttct tcagtg                                         26

<210> SEQ ID NO 44
<211> LENGTH: 23
<212> TYPE: DNA
<213> ORGANISM: Artificial Sequence
<220> FEATURE:
<223> OTHER INFORMATION: Synthetic construct: CaDof3 reverse primer.
```

-continued

```
<400> SEQUENCE: 44
ggatccccag gatgatcctc ctc                                              23

<210> SEQ ID NO 45
<211> LENGTH: 22
<212> TYPE: DNA
<213> ORGANISM: Artificial Sequence
<220> FEATURE:
<223> OTHER INFORMATION: Synthetic construct: CaPR-4 PROMOTER adaptor
      primer 1.

<400> SEQUENCE: 45
gtaatacgac tcactatagg gc                                               22

<210> SEQ ID NO 46
<211> LENGTH: 19
<212> TYPE: DNA
<213> ORGANISM: Artificial Sequence
<220> FEATURE:
<223> OTHER INFORMATION: Synthetic construct: CaPR-4 PROMOTER adaptor
      primer 2.

<400> SEQUENCE: 46
actatagggc acgcgtggt                                                   19

<210> SEQ ID NO 47
<211> LENGTH: 15
<212> TYPE: DNA
<213> ORGANISM: Artificial Sequence
<220> FEATURE:
<223> OTHER INFORMATION: Synthetic construct: PR4-P1

<400> SEQUENCE: 47
ctctttaatt tccca                                                       15

<210> SEQ ID NO 48
<211> LENGTH: 15
<212> TYPE: DNA
<213> ORGANISM: Artificial Sequence
<220> FEATURE:
<223> OTHER INFORMATION: Synthetic construct: PR4-PM2

<400> SEQUENCE: 48
ctcgggaatt tccca                                                       15

<210> SEQ ID NO 49
<211> LENGTH: 15
<212> TYPE: DNA
<213> ORGANISM: Artificial Sequence
<220> FEATURE:
<223> OTHER INFORMATION: Synthetic construct: PR4-PM3

<400> SEQUENCE: 49
ctctttccct tccca                                                       15

<210> SEQ ID NO 50
<211> LENGTH: 15
<212> TYPE: DNA
<213> ORGANISM: Artificial Sequence
<220> FEATURE:
<223> OTHER INFORMATION: Synthetic construct: PR4-PM23

<400> SEQUENCE: 50
ctcgggccct tccca                                                       15
```